United States Patent [19]

Dakka et al.

[11] Patent Number: 4,853,479
[45] Date of Patent: Aug. 1, 1989

[54] PROCESS FOR THE MANUFACTURE OF AROMATIC DICARBOXYLIC ACIDS AND DERIVATIVES THEREOF

[75] Inventors: Jihad Dakka, Bakka El Garbia; Amikam Zoran; Yoel Sasson, both of Jerusalem, all of Israel

[73] Assignees: Gadot Petrochemical Industries, Ltd., Haifa; Yissum R & D Company of the Hebrew University of Jerusalem, Jerusalem, both of Israel

[21] Appl. No.: 266,820

[22] Filed: Nov. 3, 1988

[30] Foreign Application Priority Data

Nov. 27, 1987 [IL] Israel ............................................ 84620

[51] Int. Cl.$^4$ ...................... C07C 67/39; C07C 51/265
[52] U.S. Cl. ...................................... 566/77; 562/416; 562/417
[58] Field of Search .................... 560/77; 562/416, 417

[56] References Cited

U.S. PATENT DOCUMENTS 4,158,738  6/1979  Scott et al. ............................ 562/416
4,281,179  7/1981  Komatsu et al. ..................... 562/416
4,398,037  8/1983  Takeda et al. ........................ 560/77

Primary Examiner—Werren B. Lone
Assistant Examiner—Vera C. Clarke
Attorney, Agent, or Firm—Morgan & Finnegan

[57] ABSTRACT

An improved process for the manufacture of aromatic dicarboxylic acids and derivatives thereof is described. The process is based on the reaction of a corresponding aromatic hydrocarbon in a liquid phase oxidation with an oxygen-containing gas in the presence of a phase-transfer catalyst (a) a transition metal salt (b) and traces of a polar solvent, such as water, the molar ratio between (a) and (b) being in the range of between 0.25:1 to 1.5:1. The phase-transfer catalyst is selected from the quaternary ammonium and phosphonium salts having a total carbon atoms in the range of 17 to 58, the anion bound thereto being selected from $Br^-$, $F^-$, $Cl^-$, $OH^-$, $CH_3COO^-$ and $HSO_4$. Among the aromatic dicarboxylic acids and derivatives thereof the following are mentioned: terephthalic acid; isophthalic acid and methyl terephthalate. The process is characterized by the very high conversion of the respective aromatic hydrocarbon reaching even 100%.

13 Claims, No Drawings

PROCESS FOR THE MANUFACTURE OF AROMATIC DICARBOXYLIC ACIDS AND DERIVATIVES THEREOF

The present invention relates to an improved process for the manufacture of aromatic carboxylic acids and derivatives thereof. More particularly the invention relates to an improved process for the manufacture of aromatic dicarboxylic acids and derivatives thereof at high conversions.

BACKGROUND OF THE INVENTION

It is known how to oxidize aromatic compounds possessing aliphatic substituents in the liquid phase using air or molecular oxygen. The addition of a catalyst was found to be effective for that type of oxidizing reaction. Generally the catalysts are selected from salts of metals having a variable valency such as cobalt, chromium, manganese, lead, iron, copper, nickel, vanadium, ruthenium, tungsten, cerium, molybdenum or mixtures thereof. While it is possible to produce aromatic monocarboxylic acids with relative ease, it is very difficult to produce aromatic dicarboxylic acids by one step oxidation of aromatic compounds having two oxidizable substituents.

Thus, in the known processes, the production of terephthalic acid from p-xylene is accomplished in two steps:
(a) p-xylene is reacted with oxygen in the presence of a cobalt or manganese salt, such as naphthenate, obtaining p-toluic acid, and
(b) p-toluic acid is oxidized with nitric acid producing terephthalic acid.

However the use of a two-stage process is industrially disadvantageous. This is even quite complicated in view of the resistance of p-toluic acid to oxidation. In the past thirty years, it was discovered the unexpected effect of bromide ions on the catalytic oxidation of p-xylene in the presence of carboxylic acid as solvent. It was found that the activity of a soluble cobalt catalyst is enhanced by the presence of bromide ions, so that p-xylene in acetic acid is oxidised at high temperature producing terephthalic acid. Yields of 90–95% are mentioned to be obtained. Although the purity of the product was much higher than that obtained in the previous two-stage process, it was still not high enough for use in the manufacture of polyethylene terephthalate—one of the main uses of the terephthalic acid—by a direct esterification process. Therefore, an additional purification step was required in order to obtain the desired pure product.

The major organic impurities in the oxidation product of p-xylene are p-toluic acid and p-carboxybenzaldehyde. Both are mono-functional and therefore capable of limiting the rate of polymerization and the molecular weight during polyesters manufacture. Also, p-carboxybenzaldehyde particularly leads to discoloured polymer and can not be removed by a recrystallyzation process, because it is readily occluded in the terephthalic acid. Other impurities normally present, in relatively small amounts, are: brominated acids, benzyl dicarboxylic acid and fluorene dicarboxylic acid, which also affect the polymer colour.

A large number of patents appear in the last ten years describing various improvements in the process claiming to obtain terephthalic acid at high yields and of a high purity. Thus, according to the Russian Pat. No. 1171452 (cf. C.A. 104, 68602) the oxidation of p-xylene is carried out in acetic acid at 200–215 degrees C. at a pressure of 20–26 atmospheres in the presence of Co, Mn or Ni salts and bromide compounds. In a subsequent stage the reaction product is treated with steam at 180–200 degrees C.

According to Japanese Patent Application Kokai No. 83/189135 (Cf. C.A. 100, 86267) the oxidation is carried out in 3 stages, the reaction product from the second reactor being circulated with a pump and wet grounded. In this manner it is claimed to produce terephthalic acid with a low content of 4-carboxybenzaldehyde.

According to Czech Pat. No. 218,081 (C.A. 102, 221318) terephthalic acid is obtained in the absence of organic solvents by oxidation of p-xylene with a gas containing oxygen using a Br-activated transition metal salt and N-containing compounds or transition metal complexes, benzenecarboxylic acid and water. An example of catalyst given in this patent is $Co-Br_2$-pyridine complex.

In the Japanese Patent Application Kokai No. 84/190947 (Cf. C.A 102, 167,319) it is claimed the production of a high purity terephthalic acid from p-xylene and oxygen-containing gas in acetic acid with a very low content of 4-carboxybenzaldehyde. The process consists actually of two steps, wherein in the second step the mother liquor, after separating the formed terephthalic acid, is again oxidized in the presence of a new portion of catalysts. Another Japanese Kokai No. 84/190946 (Cf. C.A. 102,167,320) describes a variation of the above process, wherein the slurry without separating the resulted product is oxidized again in another reactor.

In a theoretical review which appears in React. Kinet. Catal. Lett. Vol. 27, No. 2, 231–3, there is a communication on the use of phase-transfer catalyst for the initiation of p-xylene oxidation with molecular oxygen in p-xylene-water system. It is mentioned that the maximum absorption rates of oxygen are influenced by the nature of the onium compound. Thus in the presence of cetyltrimethyl ammonium bromide, the maximum rate of p-xylene oxidation was 1.13 compared with 1.54 when pyridine was used. It is further stipulated that the onium compounds have a significant role during the initiation of chaiss. As the reaction proceeds, "peroxide compounds are rapidly produced and they interfere in initiation and propagation steps". Accordingly it is concluded that in the later stages of p-xylene oxidation the chain initiation is not the rate determining step "the action of the quaternary salts being masked with intermediately formed peroxidic species".

It is an object of the present invention to provide a simple process for the manufacture of dicarboxylic acids and derivatives thereof by oxidation of the corresponding aromatic hydrocarbons. It is another object of the present invention to provide a simple process for the manufacture of dicarboxylic acids at high conversion. It is yet another object of the present invention to provide a simple process for the manufacture of terephthalic acid and esters thereof.

BRIEF DESCRIPTION OF THE INVENTION

The invention relates to a process for the manufacture of aromatic dicarboxylic acid and derivatives thereof from a corresponding aromatic hydrocarbon by a liquid phase oxidation of said hydrocarbon using an oxygen-containing gas, being carried out in the presence of a phase-transfer catalyst and traces of a polar solvent able to solubilize the catalyst, the process being characterized in that the oxidation reaction occurs in the presence of a catalytic system comprising:

(a) a quaternary onium salt having the general formula:

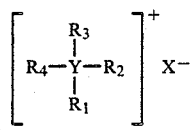

wherein:

Y may be nitrogen or phosphorus, $R_1$ is alkyl and $R_2$, $R_3$ and $R_4$ may be the same, different or interlinked, selected from alkyl, hydroxyalkyl, aryl or aralkyl group having a total number of carbon atoms in the range of between 17 and 58, and $X^-$ is selected from $F^-$, $Cl^-$, $Br^-$, $OH^-$, $CH_3COO^-$ and $HSO_4^-$, provided that when $Br^-$ is absent from the system a bromide is added, and (b) a transition metal salt, the molar ratio between (a) and (b) being in the range of between 0.25:1 to 1.5:1. The above quaternary onium salts, possessing between 17 and 58 carbon atoms, are characterized by their lipophicity which enables the extraction of the transition metal salt. The most preferable phase-transfer catalysts are the quaternary onium salts having between 20 and 48 total carbon atoms.

Typical examples of ammonium quaternary bromides and chlorides are: di-n-decyldimethyl ammonium bromide, tri-n-octylmethyl ammonium bromide, tetra-n-hexyl ammonium bromide, tetra-n-octyl ammonium bromidem, tri-n-hexyl-2-hydroxyethyl ammonium bromide, phenyl-tri-n-octyl ammonium bromide, tri-n-decyl ammonium bromide, tetra-n-dodecyl ammonium bromide, tetra-n-nonyl ammonium bromide, tetra-n-hexadecyl ammonium bromide, phenyl-tri-n-hexylammonium bromide, benzyl-tri-n-octylammonium bromide, phenyl-tri-n-decyl ammonium chloride, tri-n-dodecyl-2-hydroxyethyl ammonium chloride, n-hexadecyl-pyridinium bromide, etc. Most of these quaternary ammonium salts are also commercially available at reasonable costs. Among the quaternary phosphonium bromides and chlorides the following can be mentioned: tetra-n-hexylphosphonium bromide, tetra-n-octyl-phosphonium bromide, phenyl-tri-n-hexylphosphonium chloride, n-hexadecyl-tri-n-butylphosphonium bromide, tetra-n-hexylphosphonium bromide, etc.

Other phase transfer catalysts which may be used are for example, crown ethers (macrocyclic polyethers) which are described in details in the "Journal of the American Chemical Society", 89, 7017 (1967).

The role of the phase-transfer catalyst is to form an organic soluble adduct with a catalytic activity which does promote the oxidation reaction.

The heavy metal to be used as catalyst is generally a multivalent element, preferably selected from manganese, cobalt, molybdenum, zirconium, chromium, vanadium, ruthenium, tungsten, cerium or mixtures thereof. In particular suitable are manganese, vanadium, cobalt and ruthenium. The amount of heavy metal catalyst is not so critical and can be selected in a very broad molar ratios range such as between 1:1000 to 1:100 (heavy metal to the aromatic compound) and preferably between 1:500 to 1:200. The metal salt catalyst to be used is preferably in the hydrated form containing water of crystallization. The anion to which the heavy metal is bound, is not critical and may be selected from any inorganic or organic moiety provided that the corresponding salt can be solubilized in the reaction system. Particularly preferable are acetates, chlorides, sulfates, which are also commercially available in bulk.

The oxidation may be carried out with pure oxygen gas or preferably with a gaseous mixture containing lower concentrations of oxygen such as, for example air.

The phase-transfer catalyst has a very important role in the process according to the present invention. As known, a phase-transfer catalyst is defined as a substance which promotes reaction by transferring a substance from one phase to another phase where it undergoes the desired reaction thereby releasing the phase-transfer catalyst back into the first phase for re-use. According to the present invention it was found that the heavy metal salt is solubilized in the organic phase in the form of an onium adduct. In this manner, it catalyses the oxidation reaction.

The quaternary onium salt may be added such as, or prepared in-situ for example, in case of ammonium salt by including in the reaction system a tertiary amine and alkylating agent.

In order to initiate the reaction, the process according to the present invention must involve the addition of traces of a polar solvent such as minor amounts of water, preferably in the form of water of crystallization or as an extraneous phase. The amount of polar solvent should be sufficient to dissolve the metal salt as a saturated solution under the reaction conditions. It was found that an increase in the amount of water decreases the conversion rates of the reaction.

The process according to the present invention is characterized by its very high conversion of above 90% or even above 99%.

It was surprisingly found that the conversion of an aromatic hydrocarbon into the respective dicarboxylic acid, is correlated to the molar ratio between the phase-transfer catalyst and the heavy metal salt. It has been found that, conversions of about 60% are obtained when said ratio is 0.7, reaching this conversion after 70 minutes. Above this ratio, there is a sudden decrease in the conversion rate which can reach even a value close to zero when the above ratio is about 3:1. The preferred molar ratio of DDAB to cobalt chloride is in the range of between 0.5:1 to 0.1:1.

The use of bromide ion as a promoter in the liquid phase oxidation of xylene leads to corrosion of the apparatus by the resulted bromide and will impose corrosion-resistant equipment. According to the present invention, using the bromide ion bound to the quaternary ammonium moiety, this problem is substantially alleviated in case of the absence of an aqueous phase.

The oxidation reaction may be carried out in the absence of any solvent or optionally in the presence of an organic solvent such as halogenated hydrocarbon or aliphatic carboxylic acid when a specific mode of handling is desired. Typical examples of such solvents are acetic acid, chlorobenzene, dichlorobenzene etc. The oxidation reaction according to the present invention is carried out either batchwise or continuously at an elevated temperature in the range of 100 to 200 degrees C. and preferably in the range of 130 to 160 degrees C. Also, elevated pressure will be required e.g. in the range of 1 to 60 atmospheres (air) and preferably 10 to 25 atmospheres, corresponding to an oxygen partial pressure in the range of 2 to 15 atmospheres (g).

Among the dicarboxylic acids and derivatives thereof to be produced according to the present invention the following can be mentioned: terephthalic acid, isophthalic acid, phthalic acid, monomethyl terephthalate, 4-nitroisophthalic acid, 4-chloro-isophthalic acid, 4-bromoterephthalic acid, 4-methoxy-isophthalic acid, bromoterephthalic acid, chloro-terephthalic acid and methoxyisophthalic acid.

Among the aromatic hydrocarbons to be oxidized according to the present invention, the following can be mentioned: o-, m- and p-xylene; methyl p-toluate, 4-nitro-m-xylene, 4-chloro-m-xylene; 4-bromo-m-xylene, 4-methoxy-m-xylene, bromo-p-xylene, chloro-p-xylene, methoxy-p-xylene.

The entire process is very simple to be carried out and requires standard equipment as used for these types of products. The reactor consists of an autoclave provided with a stirrer and condenser. The autoclave has a jacket through which heated oil or cooled water are circulated, the temperatures being controlled by a thermostat. The gaseous reactants are introduced through a sparger and the out-gases through a needle valve and flow meter. Samples can be drawn through a sampling valve. The reactants: aromatic hydrocarbon, heavy metal salt, phase transfer catalyst are conveyed into the vessel followed by the introduction of air. The vessel is heated to about 130° C., whereby an increase of the pressure to about 20 atmospheres can be noticed. Upon the beginning of the oxidation reaction which is exothermic, the system heated by itself and the reactor was kept for a few hours at the about 170° C. The evolving vapors containing the hydrocarbon and water, are condensed, the hydrocarbon being recycled while the water is removed from the reaction system. In some cases when the product resulted might appear as a hard solid mass, an aliphatic carboxylic acid may be introduced to assist the handling of the product.

The aliphatic acid is subsequently recovered and recycled into the process as known in the art. Of course, the entire process can be carried out in a continuous manner which has clear advantages from an industrial point of view.

While the invention will now be described in connection with certain preferred embodiments in the following Examples it will be understood that it is not intended to limit the invention to these particular embodiments On the contrary it is intended to cover all alternatives, modifications and equivalents as may be included within the scope of the invention as defined by the appended claims. Thus the following Examples which include preferred embodiments will serve to illustrate the practice of this invention, it being understood that the particulars described are by way of example and for purposes of illustrative discussion only of preferred embodiments of the present invention.

In the Examples the concentrations and figures given are by weight unless otherwise stated.

EXAMPLE 1.

Preparation of terephthalic acid

Equipment 1 liter autoclave equipped with jacket and oil circulating thermostat, magnetic drived stirrer water cooled condenser and liquid separator, sparger for introducing gaseous reactants, outlet for gas with a needle valve and flow meter and sampling valve.

Oxidation of p-xylene 2.25 mole p-xylene (238.8 g), $6.74 \times 10^{-3}$ mole $CoCl_2 \cdot 6H_2O$ (1.606 g.) and $5.06 \times 10^{-3}$ mole, didecyl-dimethylammonium bromide (DDAB) (2.054 g.), were charged to the autoclave. The solution was heated to 135° C. with constant stirring at 750 rpm. Air was sparged through the solution at a flow rate of 3.88 l/mm (STP) while keeping the system under constant pressure of atmospheres (G).

The exothermic oxidation process started instantly causing the system to heat by itself to 171 degrees where it remained constant for six hours.

After cooling the mixture was analyzed by means of gas chromatography (using a capillary column filled with phenyl methyl silicone). It was found that the sample, after methylation of all the carboxylic groups, contains mole % terephthalic acid and about 5 mole % p-toluic acid.

EXAMPLE 2

Preparation of terephthalic acid

The experiment as in Example 1 was repeated using the same reactor, reaction conditions and amounts of reagents except the use of 2.2 g ($5.06 \times 10^{-3}$ moles) of tetrahexyl ammonium bromide as catalyst instead of the DDAB. The conversion was 100%, the product consisting of 94% terephthalic acid and 6% toluic acid as determined by gas chromatography (using the same column and method as in Example 1).

EXAMPLE 3

Preparation of terephthalic acid

The experiment as in Example 1 was repeated using the same reactor, reaction conditions and amounts of reagents except the use of 2.77 g ($5.06 \times 10^{-3}$ moles) of tetraoctyl ammonium bromide as catalyst instead of the DDAB. The conversion was 100%, the product consisting of 95% terephthalic acid and about 5% toluic acid as determined by gas chromatography (using the same column and method as in Example 1).

EXAMPLE 4

Preparation of isophthalic acid

The experiment was carried out in the same reactor as in Example 1 using the following reagents:
238.8 g of m-xylene (2.25 moles);
1.7 g of cobalt chloride hexahydrate (67 m moles);
2 g of DDAB (5 m moles).

The reagents were mixed in the autoclave at 170° C. for about 7 hours under a pressure of 22 atmospheres air at a flow rate of 3.88 l/min. After cooling the mixture was analyzed and found to consist of 51% mole isophthalic acid and 49% mole of toluic acid.

EXAMPLE 5

Preparation of methyl terephthalate

The experiment was carried out in the same reactor as in Example 1 using the following reagents:
337.5 g of methyl p-toluate (2.25 moles);
1.7 g of cobalt chloride hexahydrate (6.7 m moles);
2 g of DDAB (5 m moles).

The reagents were mixed in the autoclave at 170° C. for about 9 hours under a pressure of 24 atmospheres air, at a flow rate of 3 l/min. After cooling, the mixture was analyzed by gas chromatography and found that it consists of pure monomethyl terephthalate.

EXAMPLE 6

Preparation of terephthalic acid

The experiment was carried out in the same reactor as in Example 1 using the following reagents:

238.8 g of p-xylene (2.25 moles);
2.2 g of cobalt bromide hexahydrate (6.7 mmoles);
2.23 g of tetra-n-hexyl ammonium hydrogen sulfate (5 mmoles).

The procedure was the same as in Example 1 using the same reaction conditions.

A conversion of 100% was achieved, the product consisting of 90% terephthalic acid and 10% toluic acid.

EXAMPLE 7

Preparation of terephthalic acid

The experiment was carried out in the same reactor as in Example 1 using the following reagents:

238.8 g of p-xylene (2.25 moles);
1.6 g of cobalt chloride hexahydrate (6.7 mmoles);
4.25 g of tetra-n-dodecylammonium bromide (5 mmoles)

The procedure was the same as in Example 1 using the same reaction conditions.

A conversion of 100% was achieved, the product consisting of 92% terephthalic acid and 8% toluic acid.

We claim:

1. A process for the manufacture of aromatic dicarboxylic acid and derivatives thereof from a corresponding aromatic hydrocarbon by a liquid phase oxidation of said hydrocarbon using an oxygen-containing gas, being carried out in the presence of a phase-transfer catalyst and traces of a polar solvent able to solubilize the catalyst, the process being characterized in that the oxidation reaction occurs in the presence of a catalytic system comprising:

(a) a quaternary onium salt having the general formula:

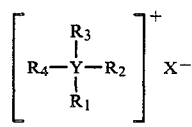

wherein:
Y may be nitrogen or phosphorus,
$R_1$ is alkyl and $R_2$, $R_3$ and $R_4$ may be the same, different or interlinked, selected from alkyl, hydroxyalkyl, aryl or aralkyl group having a total number of carbon atoms in the range of between 17 and 58, and $X^-$ is selected from $F^-$, $Cl^-$, $Br^-$, $OH^-$, $CH_3COO^-$ and $HSO_4$, provided that when $Br^-$ is absent from the system a bromide is added, and (b) a transition heavy metal salt, the molar ratio between (a) and (b) being in the range of between 0.25:1 to 1.5:1.

2. A process according to claim 1, wherein said quaternary onium salt has a total number of carbon atoms in the range of 20 to 48.

3. A process according to claim 2 wherein said quaternary ammonium salt is formed in-situ.

4. A process according to claim 1, wherein the heavy metal is selected from the group consisting of manganese, zirconium, cobalt, molybdenum, chromium, vanadium, ruthenium, tungsten, cerium or mixtures thereof.

5. A process according to claim 1, wherein the anion bound to said heavy metal is selected from chloride, bromide, acetate and sulfate or mixtures thereof.

6. A process according to claim 1, wherein the polar solvent used in the reaction is water.

7. A process according to claim 4, wherein said heavy metal salt is hydrated cobalt chloride.

8. A process according to claim 1, wherein the molar ratio between the phase-transfer catalyst and transition metal is in the range of between 0.4:1 to 1.15:1.

9. A process according to claim 1, carried out at a temperature in the range of between 130°–180° C.

10. A process according to claim 1, carried out at an oxygen partial pressure in the range of between 2 to 25 atmospheres.

11. A process according to claim 1, wherein the product obtained is terephthalic acid.

12. A process according to claim 1, wherein the product obtained is isophthalic acid.

13. A process according to claim 1, wherein the product obtained is methyl terephthalate.

* * * * *

UNITED STATES PATENT AND TRADEMARK OFFICE
CERTIFICATE OF CORRECTION

PATENT NO. : 4,853,479

DATED : August 1, 1989

INVENTOR(S) : Jihad Dakka et al.

It is certified that error appears in the above-identified patent and that said Letters Patent is hereby corrected as shown below:

In Claim 1, at Column 8, line 17, delete the word "heavy".

Signed and Sealed this

Fifth Day of March, 1991

*Attest:*

HARRY F. MANBECK, JR.

*Attesting Officer*     *Commissioner of Patents and Trademarks*